(12) United States Patent
Murphy (10) Patent No.: US 9,186,045 B2
(45) Date of Patent: Nov. 17, 2015

(54) MEDICAL SCOPE ATTACHMENT DEVICE AND SYSTEM

(71) Applicant: Christopher Murphy, Orlando, FL (US)

(72) Inventor: Christopher Murphy, Orlando, FL (US)

( * ) Notice: Subject to any disclaimer, the term of this patent is extended or adjusted under 35 U.S.C. 154(b) by 197 days.

(21) Appl. No.: 14/087,475

(22) Filed: Nov. 22, 2013

(65) Prior Publication Data

US 2015/0148593 A1      May 28, 2015

(51) Int. Cl.
*A61B 1/00*         (2006.01)

(52) U.S. Cl.
CPC .................................. *A61B 1/00158* (2013.01)

(58) Field of Classification Search
USPC .................................. 600/114, 145, 407, 409
See application file for complete search history.

(56) References Cited

U.S. PATENT DOCUMENTS

| | | | | |
|---|---|---|---|---|
| 5,681,260 | A | * | 10/1997 | Ueda .................. A61B 1/00082 128/899 |
| 6,689,049 | B1 | * | 2/2004 | Miyagi ..................... A61B 5/05 600/117 |
| 2005/0154259 | A1 | | 7/2005 | Demarco |
| 2007/0049797 | A1 | * | 3/2007 | Yoshida ............. A61B 1/00082 600/117 |
| 2013/0303847 | A1 | * | 11/2013 | Sitti ................... A61B 1/00158 600/104 |
| 2014/0251337 | A1 | * | 9/2014 | Matula, Jr. ............ A61M 16/06 128/206.21 |

* cited by examiner

*Primary Examiner* — Matthew J Kasztejna
(74) *Attorney, Agent, or Firm* — Jason T. Daniel, Esq.; Daniel Law Offices, P.A.

(57) ABSTRACT

A medical scope attachment device and system includes one or more expandable rings, each having a resilient main body and an inside diameter defining a central opening that corresponds to a dimension of a medical scope. One or more sets of opposing magnetic elements are disposed within each of the rings. The system also includes a ring attachment device having a shelf that is interposed between a pair of opposing electromagnets. The ring attachment device functioning to transition the expandable rings between an expanded and non-expanded state to receive an existing medical scope.

17 Claims, 9 Drawing Sheets

MEDICAL SCOPE ATTACHMENT DEVICE AND SYSTEM

TECHNICAL FIELD

The present invention relates generally to medical devices, and more particularly to a magnetic ring attachment system that operates to impart magnetic guidance functionality onto a medical scope in order to improve the control, orientation and/or direction of the scope during a medical procedure.

BACKGROUND

The statements in this section merely provide background information related to the present disclosure and may not constitute prior art.

There are many known devices for performing medical procedures within human patients. One of the most commonly utilized medical instruments are medical scopes which come in a wide variety of shapes, sizes, and medical uses. One such example includes a sheathed catheter which is typically introduced into a patients' body via an incision, and includes an elongated generally hollow flexible member which can be physically guided to a specific portion of the patients' body by a doctor.

The field of gastroenterology also utilizes medical scopes to perform medical imaging, diagnostics and procedures within the intestines and other related areas of a patient. One typical device used in this field is the colonoscope or endoscope, which includes a head that is disposed at a distal end of an elongated flexible/semi-flexible member. The head is inserted into the large intestine of a patient through the rectum and is moved forward through the colon via a manual pushing force.

In this regard, the head of the scope may be equipped with any number of different devices used for diagnostic or therapeutic treatments. For example, a fiber optic and/or video imaging device may be used diagnostically by a doctor for viewing the interior of the large intestine to allow visual inspection for polyps or other malformations of the intestinal wall. The head may also carry a therapeutic tool, such as a remotely controlled cauterizing loop mechanism which is capable of removing, a polyp from the mucosa of the large intestine.

In either instance, the elongated flexible or semi-flexible member of the scope typically has a hollow interior, which is in communication with an interior chamber of the scope head. The head holds the therapeutic or diagnostic device. Thus in the case of a video imaging device, the video lens and a light source may be contained in the chamber of the head and can include one or more cables that can be enclosed within the flexible elongated member. At the end of the flexible elongated member opposite the head, an eyepiece, video screen or other such instrument may be disposed for viewing the interior of the large intestine through the camera lens. Further, a control device may be disposed at the end for manually manipulating the therapeutic or diagnostic device.

In accordance with the conventional art, the elongated member of the medical scope is relatively stiff so that it may effectively push the head forward through the large intestine. Since the large intestine is not straight, but rather has a number of turns to it, it has been difficult to provide a scope which has both the stiffness necessary for pushing the head forward through the large intestine, and the flexibility to maneuver the head around the various curves of the large intestine. In this regard, it is not uncommon for traditional colonoscopes to bend into what are known as an alpha loop, N-loop and/or reverse alpha loop during the procedure. These loops in the colonoscope usually occur in the sigmoid colon, and cause great discomfort to the patient as the colonoscope is advanced further into the patient.

Moreover, in some instances, it becomes necessary to physically manipulate the position of the patient in order to aid the advancement of the scope. Such manipulation is uncomfortable to the patient, and is particularly difficult for the medical staff in instances, for example, where the patient is unconscious or heavily sedated and unable to assist with proper movement of their body.

As such, there are prior art documents which provide specialty scopes having magnetic elements disposed along the distal end which allow doctors to guide a medical scope through the patients' body with increased precision utilizing an outside magnet. One such example includes U.S. Patent Publication No. 2005/0154259, to DeMarco, the contents of which are incorporated herein by reference. In this regard, each of these methods requires the use of a specialty scope that is purpose built to perform specific medical procedures and to house the magnets. As such, each of these known specialty instruments are exceedingly expensive, and are not adaptable for use with existing hospital or physician equipment. Moreover, owing to the embedded magnetic elements, it can be exceedingly difficult to ensure the device has been effectively sterilized after each use.

Accordingly, the need exists for a magnetic scope attachment device and system which can function to secure one or more expandable and removable magnetic elements onto an existing medical scope, so as to impart magnetic guidance functionality onto the same. It would also be beneficial to provide the system in a cost effective manner that would allow the expandable magnetic elements to be discarded after each use, so as to alleviate expenses involved with sterilization.

SUMMARY OF THE INVENTION

The present invention is directed to a medical scope attachment device and system. One embodiment of the present invention can include one or more expandable rings, which are defined by a resilient main body having an inside diameter defining an opening that corresponds to a dimension of a medical scope. One or more of the expandable rings can include one or more sets of opposing magnetic elements and each of the rings can transition between an expanded and a non-expanded state. The system can also include a ring attachment device having a shelf that is interposed between a pair of opposing electromagnets.

Another embodiment of the system can include a plurality of expandable rings, each having an inside diameter that corresponds to medical scopes between 3 Fr and 34 Fr.

Yet another embodiment of the system can include an attachment device that is suited for placement of a plurality of expandable rings having different dimensions.

This summary is provided merely to introduce certain concepts and not to identify key or essential features of the claimed subject matter.

BRIEF DESCRIPTION OF THE DRAWINGS

Presently preferred embodiments are shown in the drawings. It should be appreciated, however, that the invention is not limited to the precise arrangements and instrumentalities shown.

DETAILED DESCRIPTION OF THE INVENTION

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

Identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 1.

As described herein, the term "scope" and "medical scope" can be used interchangeably to describe any type of medical instrument having an elongated, generally tubular member that is intended to be inserted within a human or animal body. Several non-limiting examples including medical catheters, sheaths, sheath catheters, endoscopes, gastroscopes, colonoscopes and arthroscopes, among many others, for example. Accordingly, the inventive concepts disclosed herein are not to be construed as limiting to any particular medical field or procedure, and can function to impart magnetic guidance to a traditional scope, as described below. As described herein, the term "magnetic guide instrument" can include any number of magnetic devices which can be used outside of a patients' body to attract and guide an expandable ring that is installed onto a medical scope and that is located within a patients' body.

Figure 1:
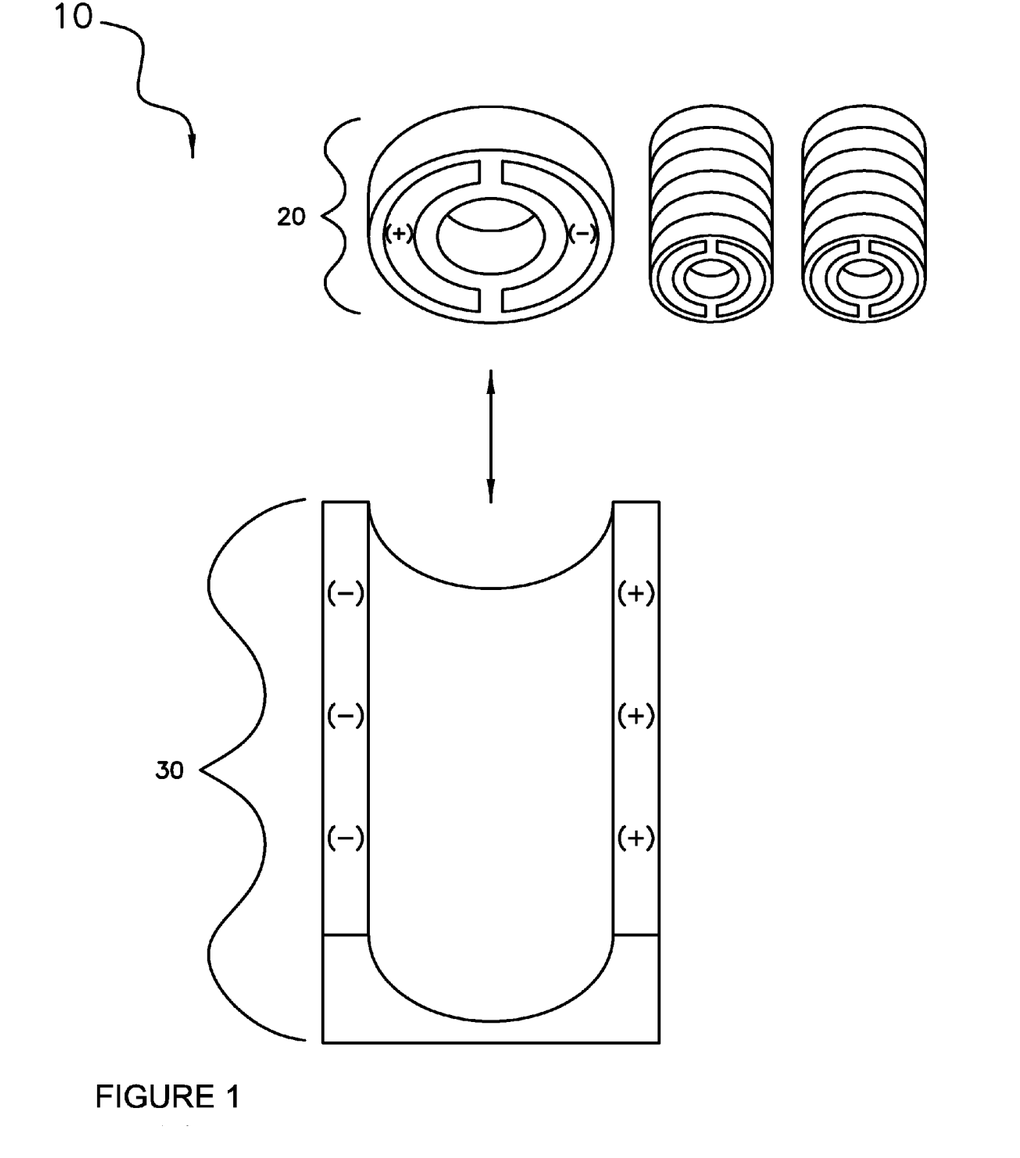
FIG. 1 is a perspective view of a medical scope attachment system that is useful for understanding the inventive concepts disclosed herein.

FIG. 1 illustrates one embodiment of a medical scope attachment system 10 that is useful for understanding the inventive concepts disclosed herein. As shown, the system 10 can include one or more expandable rings 20 and an attachment device 30 that functions to secure one or more of the rings onto an existing medical scope.

Figure 2A:
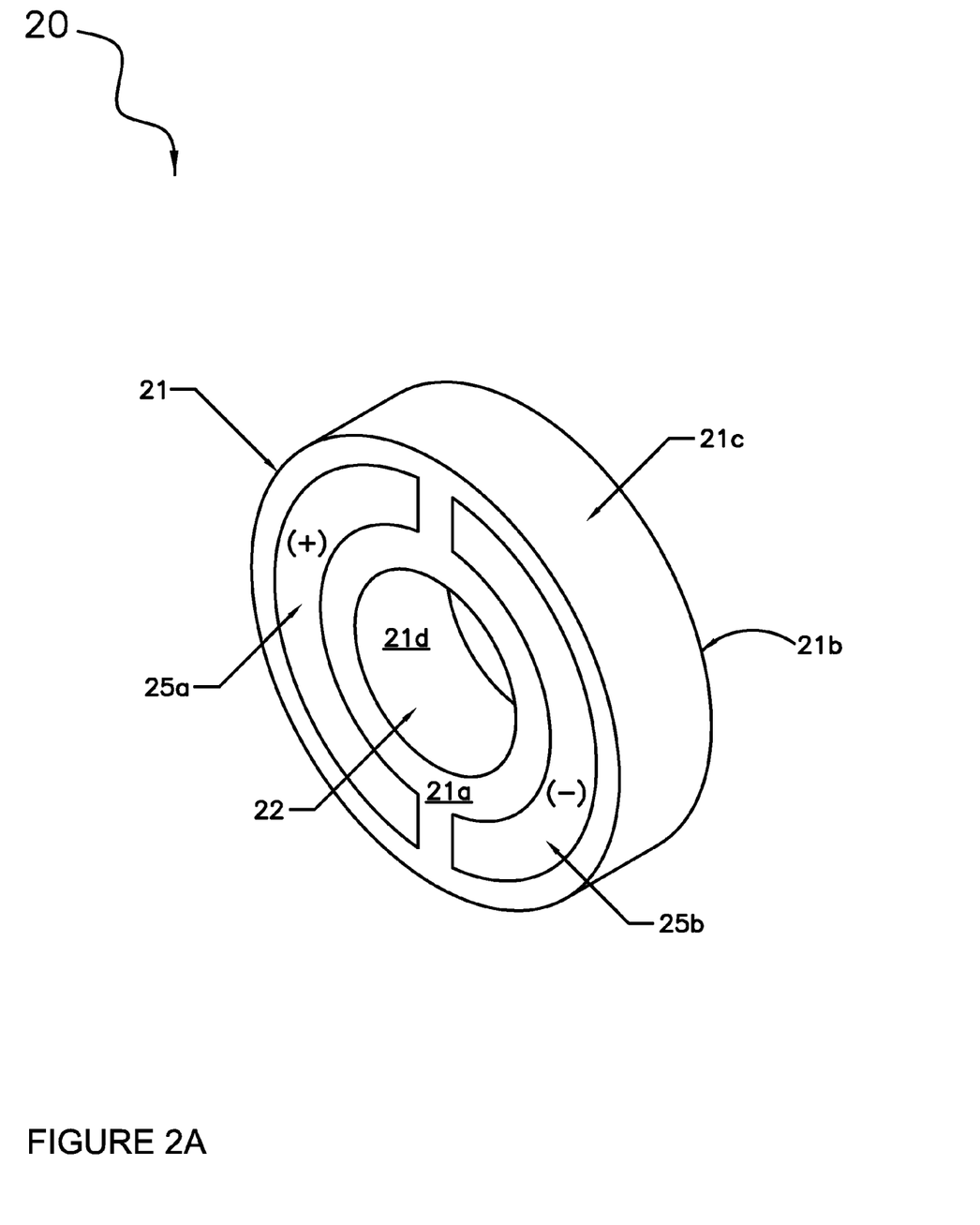
FIG. 2A is a perspective view of an expandable ring in a non-expanded state, in accordance with one embodiment of the invention.
Figure 2B:
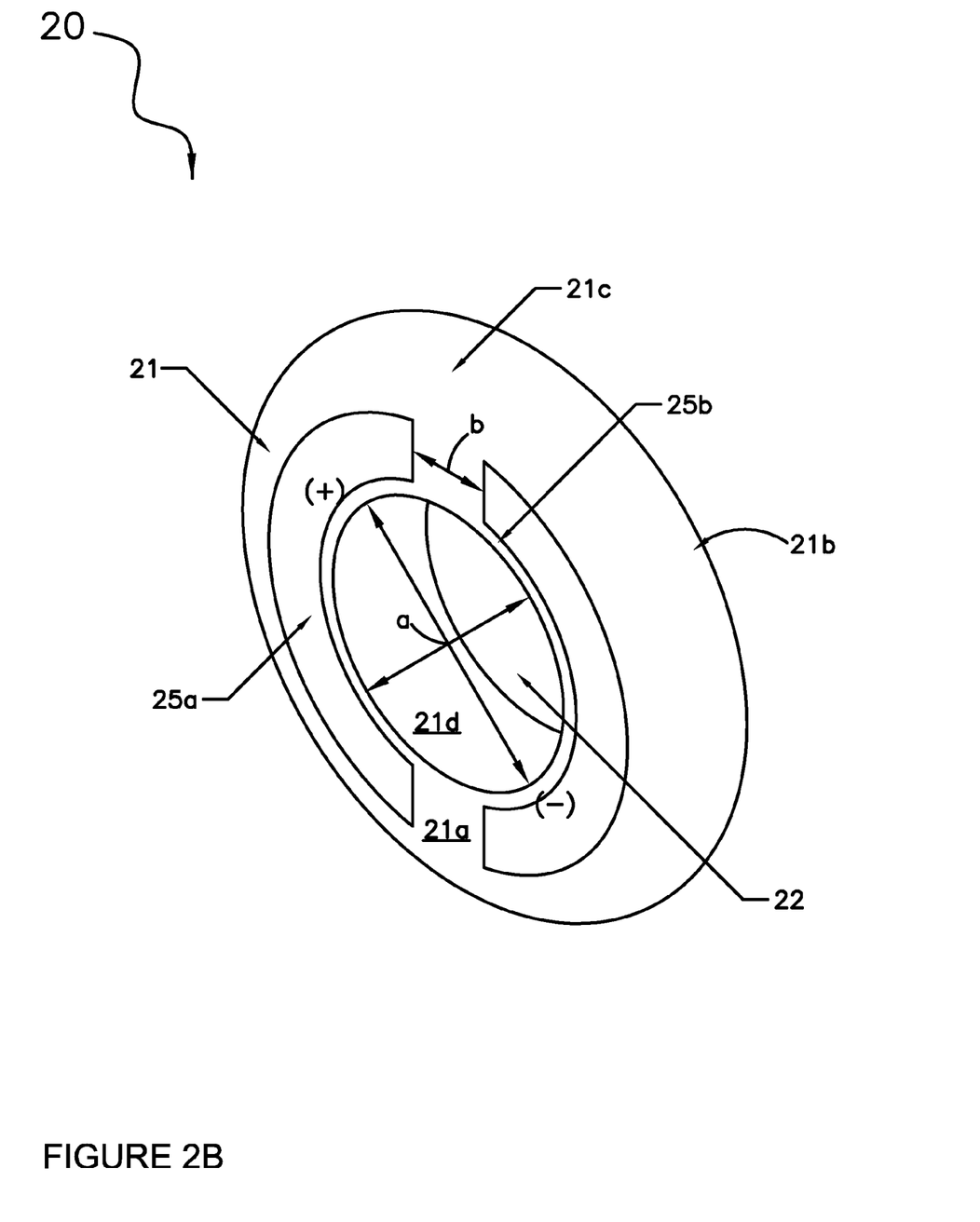
FIG. 2B is a perspective view of an expandable ring in an expanded state, in accordance with one embodiment of the invention.

FIGS. 2A and 2B illustrate one embodiment of an expandable ring 20 for use with the system. As shown, the ring 20 can include a generally circular main body 21 having a front surface 21a, a back surface 21b, an outside edge 21c having an outside diameter, and an inside edge 21d defining a central opening 22 having an inside diameter. In the preferred embodiment, the main body can be constructed from a resilient and nonreactive material such as medical grade silicone, for example, which is FDA approved and is a commonly utilized material with medical instruments, so to alleviate concerns about patient allergies. Of course, any number of other materials having excellent resilience, tensile and/or elastomeric properties can also be utilized, several non-limiting examples including plastic, polyurethane, PolyEthylene and/or Teflon/PTFE, for example.

In order to function with a traditional medical scope, it is necessary for the ring 20, and specifically the opening 22 to transition between a natural/non-expanded state, as illustrated in FIG. 2A, and an expanded/stretched state, as illustrated in FIG. 2B (see arrow a). Such a feature allows the distal end of a scope to be inserted through the opening 22 while the ring is in an expanded state. Then, upon returning to the non-expanded state, the smaller diameter of the opening 22 imparts a strong compression force against the inserted scope, thereby preventing separation of the ring and scope when the device is in use.

Although sometimes measured utilizing the French Gauge (Fr) system, medical scopes are typically referred to by their outside diameter in millimeters (e.g., a 5 mm scope or a 20 mm scope). In this regard, the most commonly utilized medical scopes will typically include an outside diameter of between, 1 mm and 25 mm. However, scopes having smaller and larger diameters are also contemplated. As such, the following discussion will refer to particular examples of the expandable ring as including diameters of specific millimeters. However, it is to be understood that each of the expandable rings can be constructed to accommodate medical instruments having any number of different diameters, regardless of the specific measurement system discussed.

As noted above, medical scopes are constructed with known and predetermined outside diameters. In this regard, it is preferred that each ring 20 be constructed to include dimensions that are complementary to the size of a specific medical scope onto which the ring is to be installed. Utilizing the above noted example of medical scopes being between 1 and 25 mm, one non-limiting embodiment can include a plurality of rings wherein each ring 20 is constructed to include an inside diameter of between approximately 0.5 mm and 24 mm in a non-expanded state, and can also be constructed to expand to include a diameter of between approximately 1.5 mm and 30 mm, respectively, in an expanded state. Such dimensions being suitable for accommodating the most commonly sized traditional medical scopes having an outside diameter of between 1 mm and 25 mm, respectively. Of course, the expandable rings 20 are not limited to this range, as one or more of these rings can include dimensions and/or diameters that are greater or less than those described above.

For purposes of illustration only, one non-limiting example of the ring 20 can include an inside diameter of 5 mm, and an outside diameter of 10 mm in the non-expanded state. However, when engaged by the attachment device 30 described below, the ring 20 can expand to include an inside diameter of 8 mm and an outside diameter of 13 mm. Such dimensions being suitable for allowing the ring 20 to receive and securely attach to a medical scope having a size of between approximately 5.3 mm and 7.3 mm (i.e., between 16 Fr and 22 Fr). Of course, these dimensions are for illustrative purposes only, as the inventive concepts described herein can be applied to scopes having a wide variety of shapes, sizes (i.e., diameter of the tubular member), materials and uses.

As shown, one or more sets of opposing magnetic elements 25a and 25b can be encompassed within the main body 21 of each ring 20. In one preferred embodiment, each of the elements 25a and 25b can be constructed from a semicircular shaped Neodymium rare earth magnet having opposing polarities (+) and (−), respectively. In this regard, the opposing polarities of the magnetic elements can function to maintain the ring 20 in the non-expanded state. As such, when the ring is installed onto a medical scope, the attraction between the magnetic elements, along with the resilient nature of the main body itself in a non-expanded state will create a strong compression force against the scope that will prevent the installed ring 20 from falling off the scope during a medical procedure.

Although described above as including semicircular Neodymium magnets, other shapes and magnetic materials are also contemplated. For example, the magnetic elements can include any number of different materials forming a magnet or that are attracted by a magnet, several non-limiting examples including iron, nickel, cobalt, gadolinium, neodymium, samarium, ferrite, and alnico, for example. Each of these elements being suitable for being positioned within the ring body 21 and susceptible to the attractive force of a magnetic guide instrument.

Figure 3A:
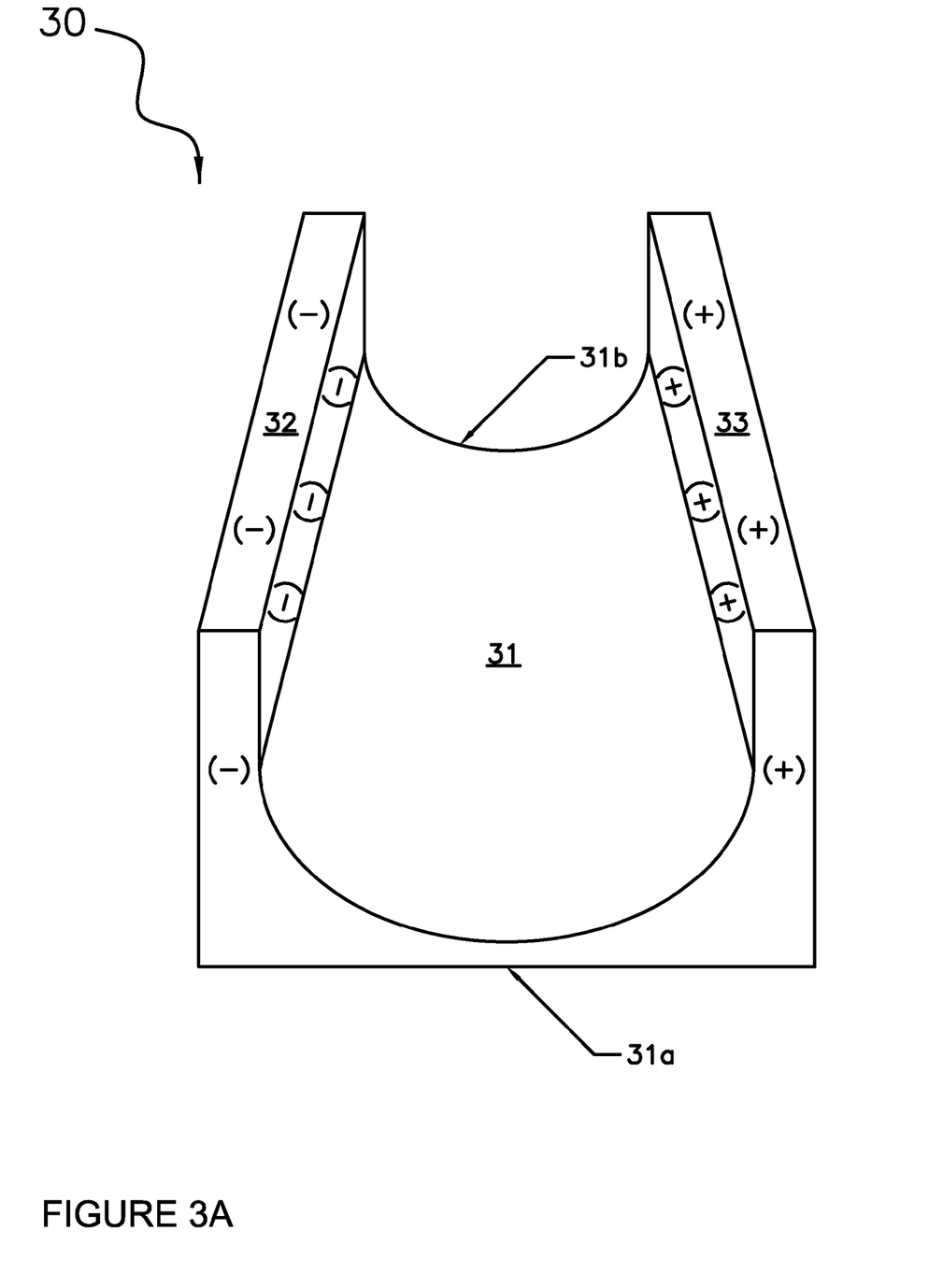
FIG. 3A is a front perspective view of a ring attachment device for use with the expandable rings of FIGS. 2A and 2B.

FIG. 3A illustrates one embodiment of an attachment device 30 which can be utilized to secure one or more expandable rings 20 onto a medical scope. As shown, the device 30 can include a shelf 31 that is interposed between a pair of elongated electromagnets 32 and 33.

In the preferred embodiment, the shelf 31 can be constructed from a nonmagnetic material such as plastic, and can have a generally hyperbola shape that includes a wide front end 31a that tapers to a narrow back end 31b. In one embodiment, the wide front end can include a width (e.g., the distance between the opposing electromagnets 32 and 33) that is suitable for receiving an expandable ring that is sized to fit medical scopes of 34 Fr. Likewise, the back end 31c can include a width that is suitable for receiving an expandable ring that is sized to fit medical scopes of 3 Fr. In this regard, the space between the front end 31a and back end 31b can accommodate rings that are sized to fit medical scopes ranging between 4 and 33 Fr. Of course, any number of other sizes is also contemplated.

The electromagnets 32 and 33 can be powered by any suitable power source and controller (not illustrated), and can include opposite polarities (−) and (+) respectively. Electromagnets are extremely well known in the art, and function to create a strong magnetic field which attracts magnetic elements and/or magnets that have an opposite polarity. In this regard, each of the electromagnets 32 and 33 can function to create a sufficient magnetic attraction with the magnetic elements 25a and 25b, respectively, of the ring 20 so as to transition the ring from the non-expanded state to the expanded state described above, when the electromagnets 32 and 33 are in operation. Although illustrated as single elements, this is for ease of illustration, as each of the electromagnets 32 and 33 can include any number of individual electromagnetic and/or magnetic elements working together to perform the functionality of the illustrated elements 32 and 33.

In this regard, although the electromagnets are illustrated as including generally rectangular shapes, this is also for illustrative purposes only. To this end, each of the electromagnets 32 and 33 can include any number of different shapes and sizes suitable for engaging the expandable rings as described above. For example, each of the electromagnets can also include one side that has a generally semicircular shape so as to engage the ring uniformly across the outer diameter of the expandable ring. When so constructed, the shelf 31 can be much smaller and function merely to connect the opposing semicircular electromagnets together.

Figure 3B:
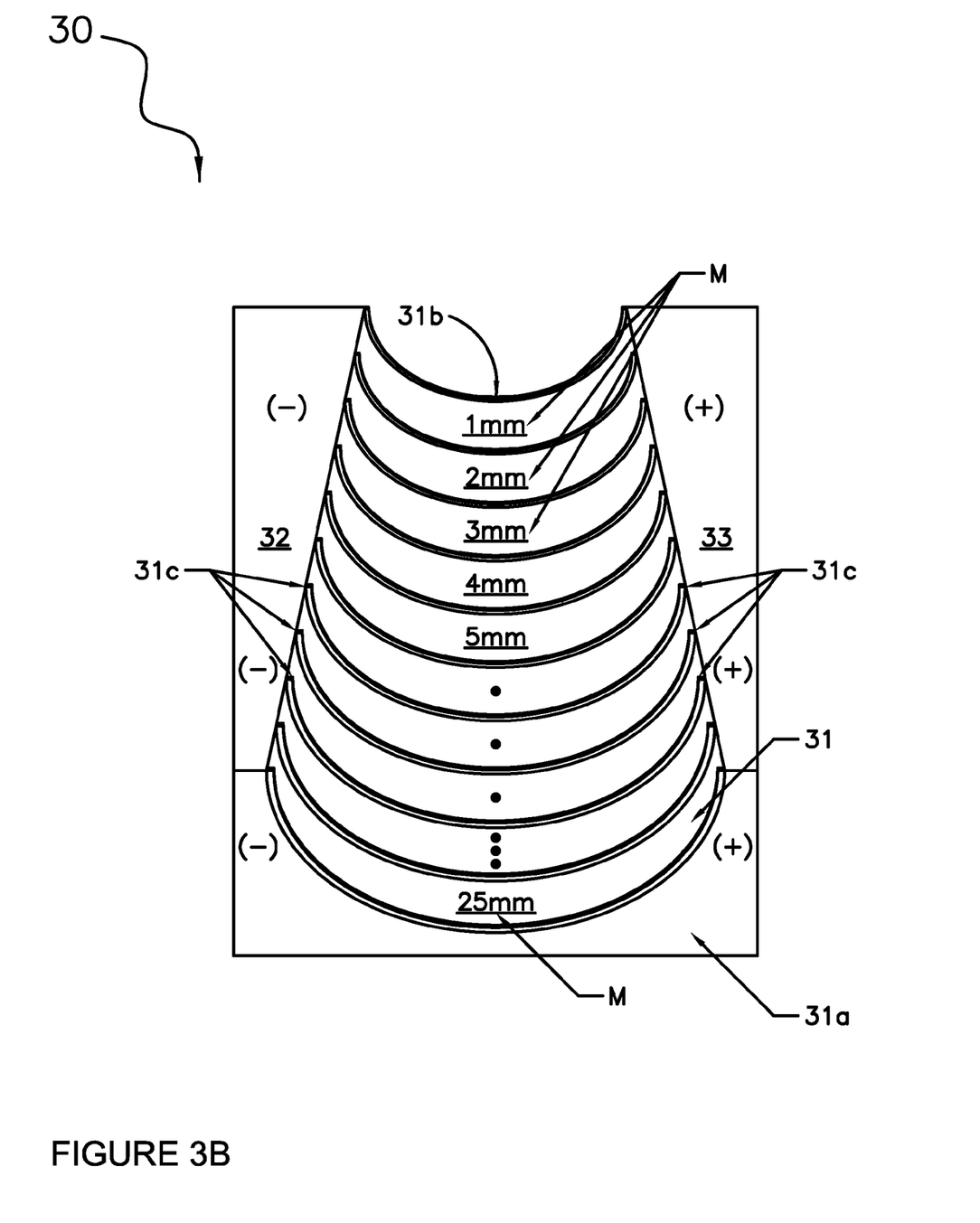
FIG. 3B is a perspective view of another ring attachment device, in accordance with one embodiment of the invention.

FIG. 3B illustrates another embodiment of the attachment unit 30 that further includes a plurality of raised lip sections 31c that are disposed along the shelf member 31 and function to provide individual receptacles for placement of expandable rings of different sizes. In one embodiment, the shelf 31 can include a plurality of receptacles, each having a marking M to indicate placement of a ring 20 that is sized to fit a medical instrument having the size indicated by the marking. Of course, any number of other sizes, units of measurements and/or markings is also contemplated.

Figure 3C:
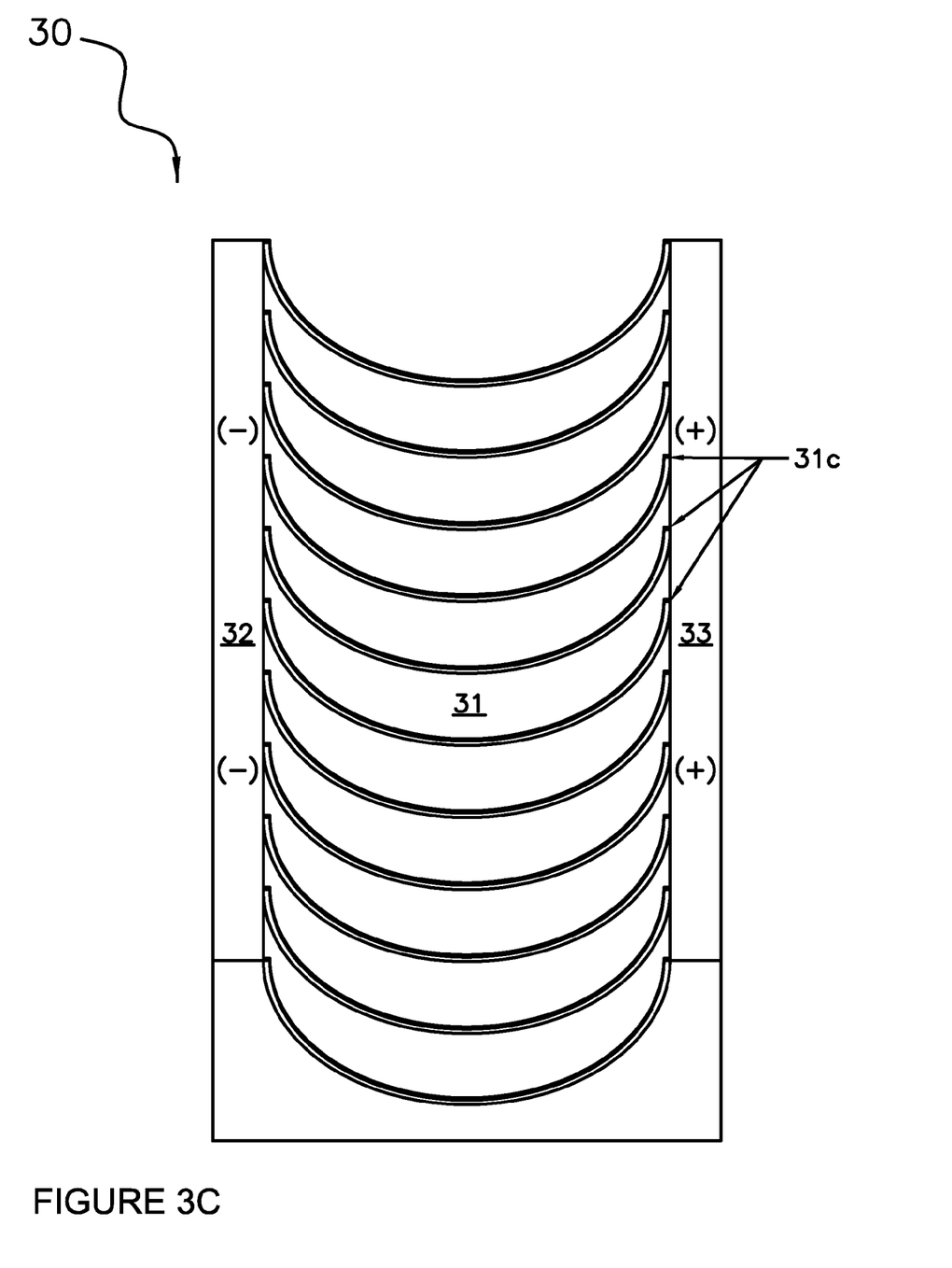
FIG. 3C is a perspective view of yet another ring attachment device, in accordance with one embodiment of the invention.

FIG. 3C illustrates another embodiment of the attachment device 30 that includes a fixed width shelf 31 for accommodating one or more rings having identical dimensions. Such a feature can be beneficial to medical facilities that typically work with a single type of scope having a single measurement.

Although not illustrated, each of the expandable rings 20 can be provided with any number of different tools in order to facilitate easy handling by a user and loading within the attachment device 30. In one such example, each of the rings 20 can be supplied from a manufacturing center having an elongated non-magnetic shaft disposed within the central opening 22.

Figure 4A:
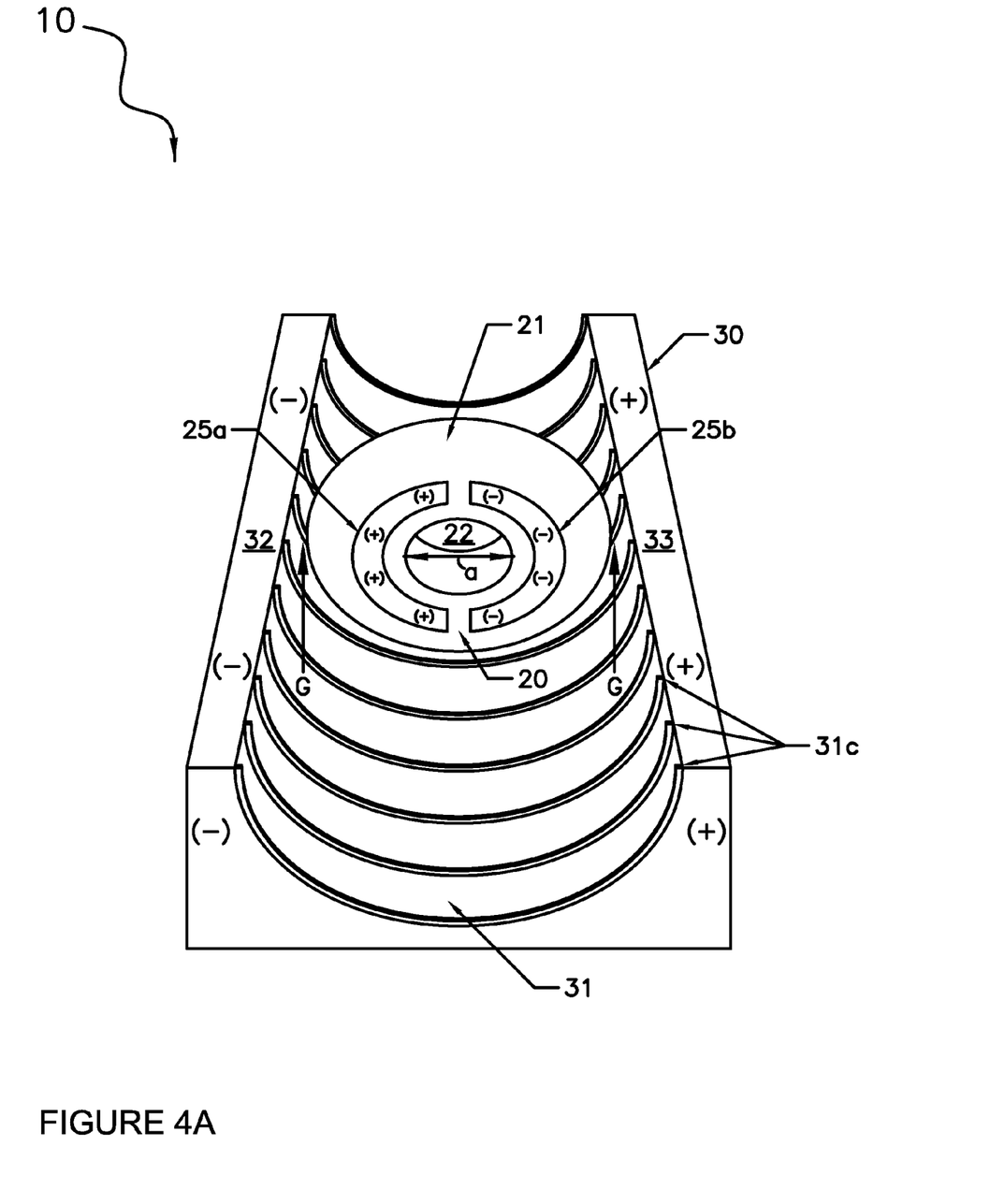
FIG. 4A is a perspective view of the medical scope attachment system in operation, in accordance with one embodiment of the invention.
Figure 4B:
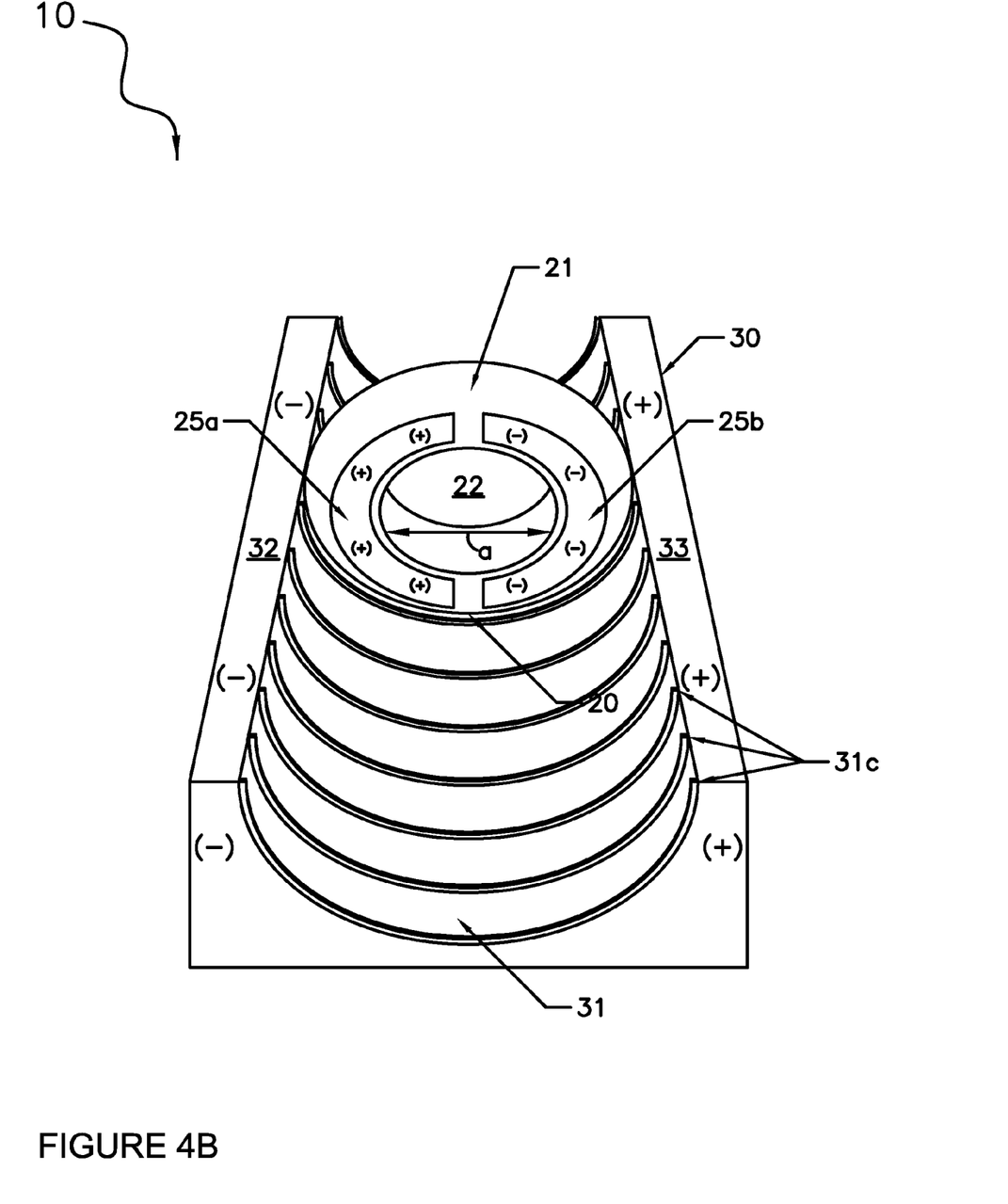
FIG. 4B is another perspective view of the medical scope attachment system in operation, in accordance with one embodiment of the invention.
Figure 4C:
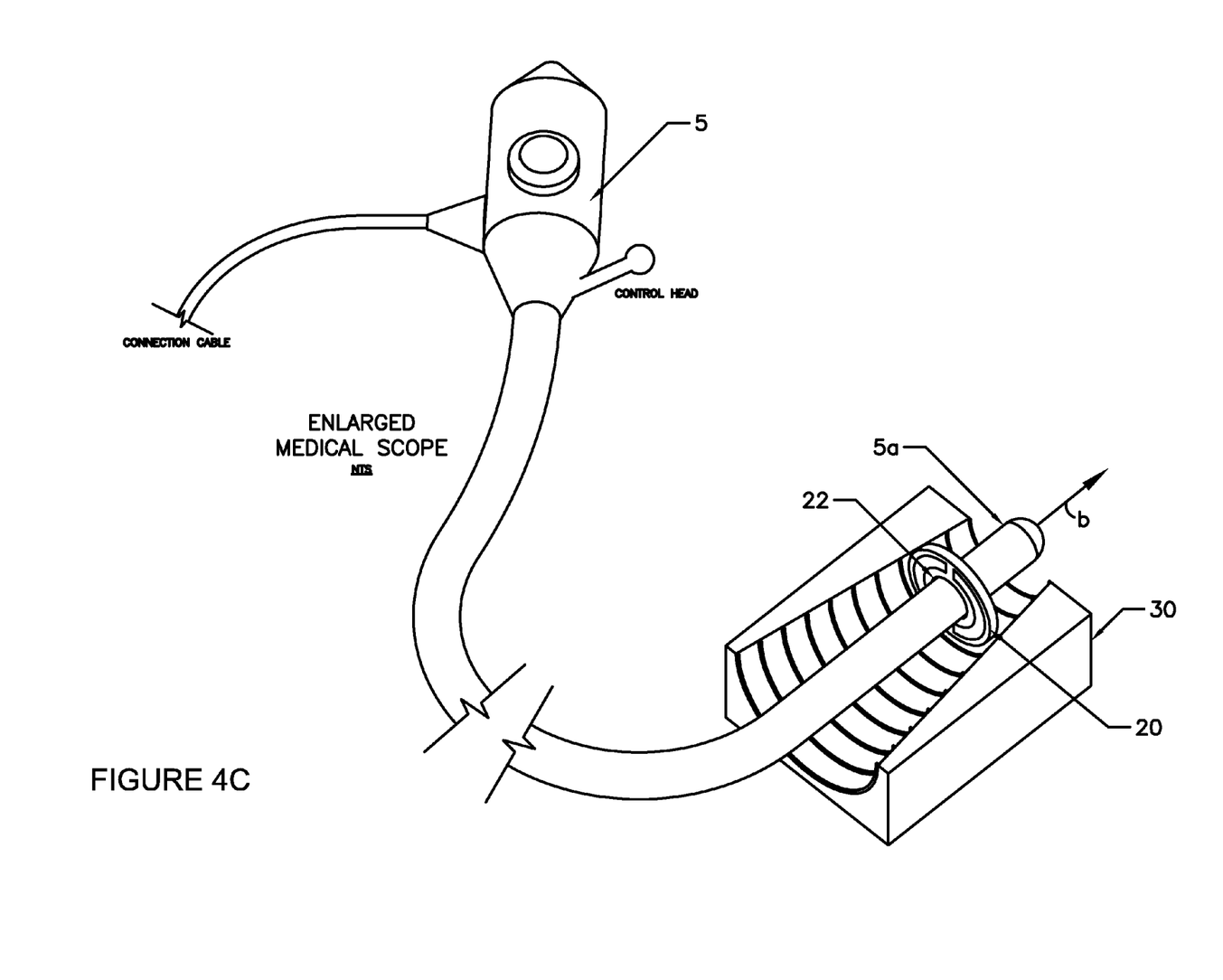
FIG. 4C is a perspective view of the medical scope attachment system in operation with a traditional medical scope, in accordance with one embodiment of the invention.

FIGS. 4A-4C illustrate one embodiment of the system 10 in operation. As shown, a ring 20 can be positioned onto the shelf 31 of the attachment device 30 wherein the positive polarity of the magnetic element 25a is located adjacent to the negative polarity of the electromagnet 32, and the negative polarity of the magnetic element 25b is positioned adjacent to the positive polarity of the electromagnet 33. As shown, when in this position, a slight gap G exists between the ring 20 and the electromagnets.

As shown in FIG. 4B, the electromagnets 32 and 33 can then be energized so as to transition the ring 20 into an expanded state. In this regard, the electromagnets can function to physically pull each of the magnetic elements 25a and 25b away from each other, so as to increase the diameter of the opening 22 as discussed above, and as illustrated by arrow a.

As shown in FIG. 4C, when the ring 20 is in an expanded state, the distal end 5a of a medical scope 5 can be inserted through the opening 22 until the ring is positioned at a desired location. In this regard, it is notable that the open design of the attachment unit 30 allows the elongated body of the scope 5 to pass through both the ring 20 and the attachment unit 30 so as to allow the ring to be secured onto the scope 5 at any position (i.e., distal or proximate). When so positioned, the electromagnets 32 and 33 can be de-energized so as to allow the ring 20 to contract and compress against the scope 5. As noted above, owing to the natural magnetic attraction of the magnetic elements 25a and 25b, along with the resilient nature of the main body 21, the ring 20 can be securely positioned onto the medical scope with a sufficient force so as to not become removed during a surgical procedure.

Finally, once attached to the scope, a physician can guide the magnetic ring 20 to a desired location within a patient using any number of external magnets in accordance with known medical procedures.

Accordingly, the inventive concepts disclosed herein can function to transition any number of existing medical scopes into magnetically guided medical scopes for use in a variety of medical procedures. Further, owing to the low manufacturing cost of the expandable rings 20 when compared to an entire specialty scope, and the sterilization/high level disinfection costs of the same, it becomes possible to utilize the rings in a disposable manner wherein the ring is discarded after one use.

As described herein, one or more elements of the magnetic scope attachment system 10 can be secured together utilizing any number of known attachment means such as, for example, screws, glue, compression fittings and welds, among others. Moreover, although the above embodiments have been described as including separate individual elements, the inventive concepts disclosed herein are not so limiting. To this end, one of skill in the art will recognize that one or more individual elements of each of the expandable ring 20 and/or the attachment device 30 may be formed together to form continuous elements, either through manufacturing processes, such as welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A medical scope attachment system, said system comprising: at least one expandable ring that includes a generally circular main body having an outside diameter and an inside diameter that defines a central opening, said ring being constructed from a resilient material that is approved for insertion within a human body and said inside diameter corresponds to an outside diameter of a medical scope; said ring being constructed from a resilient material, and one or more sets of opposing magnetic elements disposed within the main body of the ring; and a ring attachment device that includes a pair of opposing electromagnets, and a shelf that is interposed between the pair of electromagnets, wherein the shelf functions to receive one or more of the expandable rings, and the pair of opposing electromagnets function to engage the pair of opposing magnetic elements to transition an inserted ring between an expanded and a non-expanded state.

2. The device of claim 1, wherein the inside diameter of each of the one or more rings corresponds to a known diameter of a distal portion of a medical scope.

3. The device of claim 2, wherein each of the one or more rings are constructed to include dimensions that are complementary to one or more medical scopes having a known diameter.

4. The device of claim 3, wherein the shelf is constructed to form a generally hyperbola shape having a wide front end and a narrow back end.

5. The device of claim 4, wherein the front end of the shelf includes a width that is suitable for receiving an expandable ring that is sized to fit a medical scope having a first diameter.

6. The device of claim 5, wherein the back end of the shelf includes a width that is suitable for receiving an expandable ring that is sized to fit a medical scope having a second diameter, said second diameter being less than said first diameter.

7. The device of claim 1, wherein the pair of opposing magnetic elements consist of one or more sets of semicircular magnets each having an opposite polarity, said magnets including a construction suitable for being acted upon by a magnetic guide instrument when the expandable ring is inserted within a patients' body.

8. The device of claim 7, wherein the opposing magnetic elements function to maintain the ring in a non-expanded state when not engaged by the ring attachment device.

9. The device of claim 1, wherein each of the pair of opposing magnetic elements are constructed from metal that is attractive to an outside magnetic force.

10. The device of claim 1, wherein each of the one or more expandable rings are constructed from a nonreactive material that is approved for insertion within a human body.

11. The device of claim 1, wherein each of the one or more expandable rings are constructed from medical grade silicone.

12. The device of claim 1, wherein the shelf is constructed from a non-magnetic material.

13. The device of claim 1, wherein the shelf is constructed to form a generally hyperbola shape having a wide front end and a narrow back end, said shelf including a width suitable for receiving expandable rings of varying dimensions.

14. The device of claim 1, wherein the shelf is constructed to form an elongated straight member having a curved surface area for receiving one or more expandable rings having an identical dimension.

15. The device of claim 1, wherein the shelf further includes a plurality of raised lip sections that function to provide a plurality of individual receptacles for receiving individual expanding rings.

16. The device of claim 1, wherein the attachment device includes an open front end and an open back end that functions to allow placement of an expandable ring onto a medical scope at any location.

17. An expandable ring for attachment onto a medical scope and for use with a ring attachment device having a pair of opposing electromagnets, and a shelf that is interposed between the pair of electromagnets, said ring comprising:

a generally circular main body having an outside diameter and an inside diameter that defines a central opening, said ring being constructed from a resilient material that is approved for insertion within a human body and said inside diameter corresponds to an outside diameter of a medical scope; and one or more sets of opposing magnetic elements disposed within the main body of the ring, said magnetic elements including a generally semicircular shape and having opposite magnetic polarities, wherein the outside dimension of the ring is complementary to a width of the shelf of the attachment system, and the opposing magnetic elements function to engage the pair of electromagnets to transition between an expanded and a non-expanded state.

* * * * *